United States Patent [19]

Hamilton

[11] Patent Number: 5,256,814
[45] Date of Patent: Oct. 26, 1993

[54] EXCITATORY AMINO ACID ANTAGONISTS

[75] Inventor: Greg S. Hamilton, Catonsville, Md.

[73] Assignee: Scios Nova Inc., Mountain View, Calif.

[21] Appl. No.: 919,633

[22] Filed: Jul. 24, 1992

Related U.S. Application Data

[63] Continuation of Ser. No. 624,168, Dec. 7, 1990, abandoned.

[51] Int. Cl.$^5$ .............. C07F 9/38; A61K 31/66
[52] U.S. Cl. .................................. 562/11
[58] Field of Search ................... 562/11; 514/114

[56] References Cited

U.S. PATENT DOCUMENTS 4,761,405  8/1988  Rzeszotarski et al. ............... 558/190

OTHER PUBLICATIONS

Ferkany, J. W. et al., Pharmacological Profile of NPC 12626, A Novel, Competitive N-Methyl-D-Aspartate Receptor Antagonists J.P.E.T. 250:100–109 (1989).
Willets, J. and R. L. Balster, Pentobarbital-Like Discriminative Stimulas Effects of N-Methyl-D-Asparate Antagonists, J.P.E.T. 249:438–443 (1989).
Syldatk, C. et al., *Abstract & Review Only* Microbial, Enantioselective Hydrolysis of D,L-5-Monosubstituted Hydantoins for the Production of D-N-L-Amino Acids, Biotech Forum: 9–19 (1986).
Olivieri, R. et al., Mictobial Transformation of Racemic Hydantoins to D-Amino Acids, Biotechnololgy and Bioengineering 23: 2173–2183 (1981).

Primary Examiner—José G. Dees
Assistant Examiner—B. Frazier
Attorney, Agent, or Firm—Vanessa L. Appleby; Vincent Fabiano; Pete Shearer

[57] ABSTRACT

An unexpectedly more potent isomer of 2-amino-4,5-(1,2-cyclohexyl)-7-phosphonoheptanoic acid, a known excitatory amino acid antagonist, pharmaceutical compositions including this isomer and methods of using this isomer to antagonize excitatory amino acid receptors.

3 Claims, No Drawings

EXCITATORY AMINO ACID ANTAGONISTS

This application is a continuation of copending application Ser. No. 07/624,168, filed Dec. 7, 1990, and now abandoned.

BACKGROUND OF THE INVENTION

1. Field of the Invention

The present invention relates to one of the eight isomers of 2-amino-4,5-(1,2-cyclohexyl)-7-phosphonoheptanoic acid, a compound which is an excitatory amino acid (EAA) neurotransmitter receptor antagonist useful as an anticonvulsant, analgesic, cognition enhancer, and neuroprotectant. When compared to the remaining seven ACPA isomers, the invented isomer is unexpectedly more potent in in vitro receptor binding assays and in in vivo efficacy studies.

2. Description of Related Information

The compound 2-amino-4,5-(1,2-cyclohexyl)-7-phosphonoheptanoic acid (ACPA) was described as an excitatory amino acid receptor antagonist in U.S. Pat. No. 4,761,405 which issued on Aug. 2, 1988. ACPA is a compound that has three asymmetric carbon atoms and thus eight stereoisomers. In U.S. Pat. No. 4,761,405 ACPA is reported as a racemic mixture of the eight isomers, and the in vitro and in vivo data presented to show efficacy as an excitatory amino acid receptor antagonist was generated by testing the racemic mixture. This patent does not include data showing relative activities of any of the eight isomers.

DETAILED DESCRIPTION OF THE INVENTION

The presently invented compound that is active as an excitatory amino acid receptor antagonist is the 2R, 4R, 5S isomer of ACPA that is substantially free from the other ACPA isomers. Substantially free is defined to mean at least about 95% pure.

The starting material for preparation of the novel compound of the invention is 1R, 2S- Methyl (hydrogen)-1,2-cis-cyclohex-4-ene diacetate 2. This compound is prepared from the known meso diester via enantioselective enzymatic hydrolysis utilizing the enzyme porcine pancreas lipase. Y. Nago, et al., *J. Org. Chem.* (1985), 50, 4072. The use of this enzyme to obtain the chiral product 2 is known in the literature. Y. Nago, et al., *Chem. Lett.* (1989) 239.

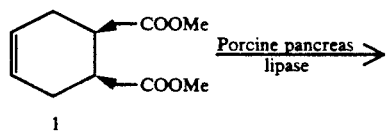

1

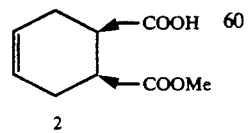

2

The preparation of the compound of the invention starting from the known compound 2 is summarized in Scheme I.

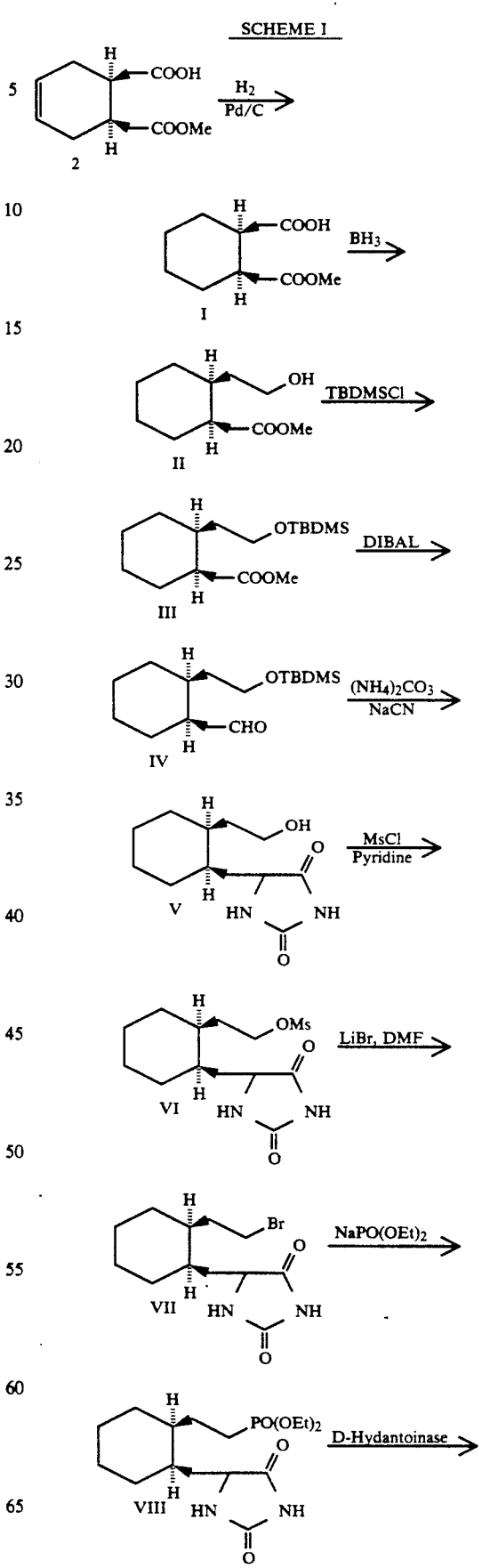

-continued
SCHEME I

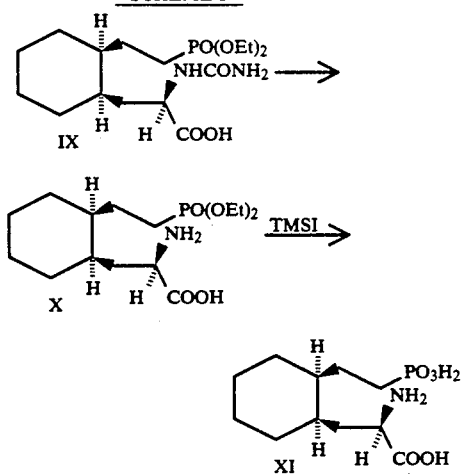

After reduction of the double bond in 2 with hydrogen in the presence of a palladium catalyst, diborane is used to selectively reduce the carboxylic acid group to the corresponding hydroxyethyl side chain (Compound II). The alcohol is converted to its tert-butyldimethylsilyl ether III, and the ester moiety is reduced to the corresponding aldehyde using disobutylaluminum hydride. Aldehyde IV is then converted to hydantoin V by reaction with sodium cyanide and ammonium carbonate; the silyl group is removed from the oxygen during this process. The alcohol is converted first to methanesulfonyl derivative VI by treatment with methanesulfonyl chloride and pyridine; compound VI is then reacted with lithium bromide in N,N-dimethylformamide to obtain bromide VII. Bromide VII is reacted with the sodium salt of diethylphosphite in tetrahydrofuran to obtain phosphonate VIII. Enzymatic hydrolysis of VIII with the enzyme D-hydantoinase obtained from cells of Agrobacterium radiobacter results in conversion to carbamoyl acid IX. R. Oliver, et al., *Biotechnol. Bioengin* (1981) 23, 2173; J. Takahashi, et al., *J. Ferment Technol.* (1979) 57, 328. The free amino acid X obtained from chemical hydrolysis of IX is then deprotected with iodotrimethylsilane to obtain the compound of the invention, 2R, 4R, 5S ACPA.

An alternate method for synthesizing the invented isomer also can be used and is summarized in Scheme II.

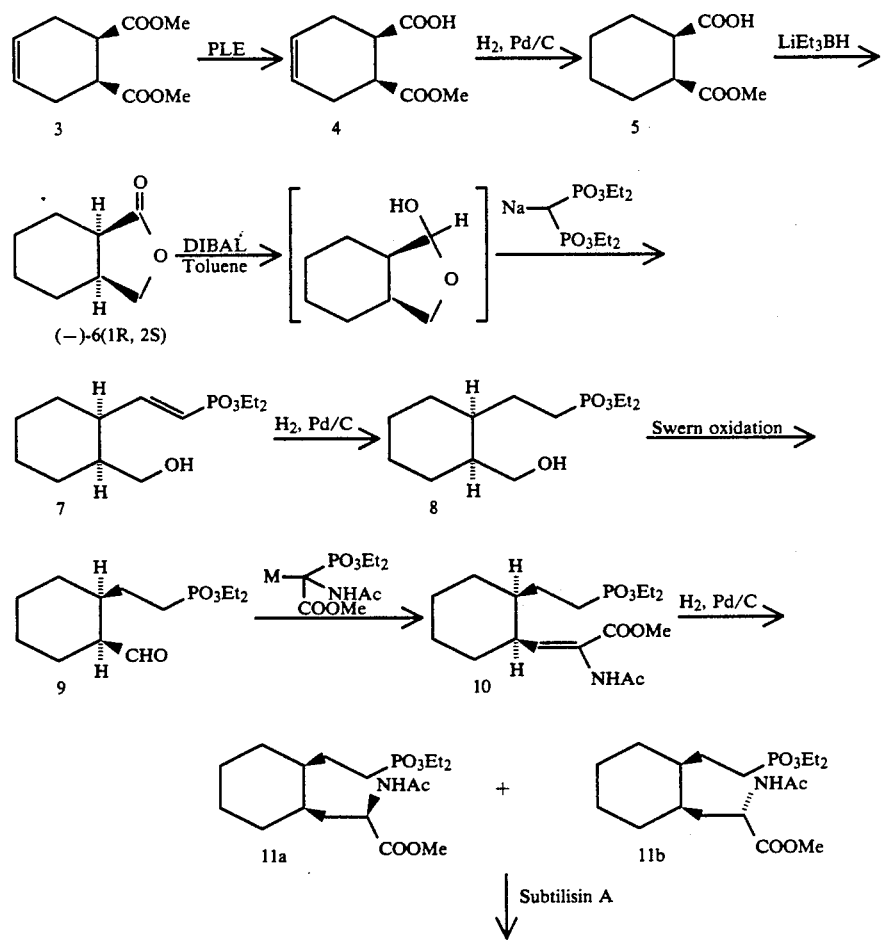

SCHEME II

SCHEME II

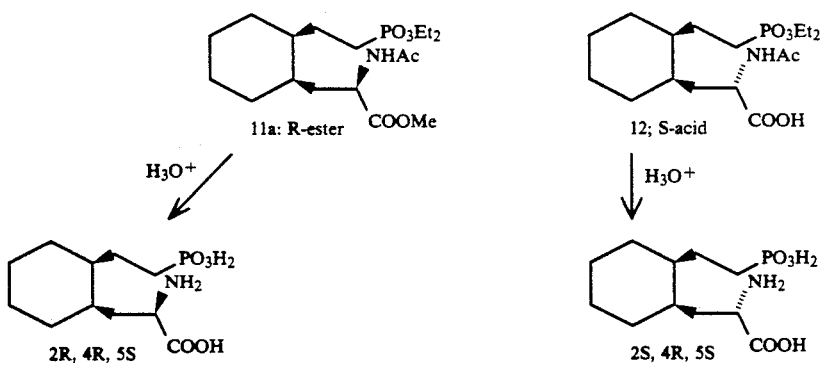

This method begins with the hydrolysis of diester 3 using pig liver esterase (PLE), a reaction known to yield the 1S, 2R half-ester in 97% enantiomeric excess. S. Kobayashi, et al., *Tet. Lett.* (1984) 25, 2557. Selective reduction of the carboxylate ester with lithium triethylborohydride afforded the enantiomerically pure (−)-1R, 2S lactone 6. The optical rotation of this lactone was identical to that reported in the literature. I. J. Jakovac, et al., *J. Am. Chem. Soc.* (1982) 104, 4659.

Reduction of 6 to the lactol and subsequent reaction with the sodium salt of diethyl methylenebisphosphonate provided the vinylphosphonate 7 which was reduced to phosphonoethyl compound 8. The hydroxyl function was oxidized by Swern's method to aldehyde 9. A final Wittig reaction was utilized to incorporate the glycine moiety and complete the skeleton. In the presence of the phosphonate moiety this reaction has consistently produced the adduct 10 in yields of ca. 7%. Reduction of the double bond in 10 provided samples of diastereomers 11a and 11b. This mixture was resolved by using Subtilisin A, an esterase, to selectively hydrolyze the S amino ester of the R,S pair; the resulting S-acid 12 was easily separated from unreacted R-ester 11a by extractive techniques. The two compounds thus obtained were hydrolytically deprotected to deliver samples of two pure cis isomers of ACPA; the 2R, 4R, 5S isomer and the 2S, 4R, 5S isomer. HPLC analysis of these compounds against the pure isomers obtained via HPLC separation of the mixtures led to the tentative identification of the 2R, 4R, 5S isomer as isomer A, the active antagonist.

Pharmaceutically acceptable acid and base addition salts of the invented isomer are formed with strong moderately strong organic or inorganic acids or bases by known methods. Exemplary of the salts included in this invention are maleate, fumarate, lactate, oxalate, methanesulfonate, ethavesulfonate, bezenesulfonate, tartrate, citrate, hydrochloride, hydrobromide, sulfate, phosphate, quinate, and nitrate salts.

Also included in the invention are pharmaceutical compositions comprising the invented isomer of ACPA and suitable carriers in pharmaceutical dosage forms such as capsules, tablets, injectable preparations, ointments, creams, topical reservoirs such as transdermal patches, and suppositories. Solid or liquid carriers can be used. Solid carriers include starch, lactose, calcium, sulfate, dehydrate, terra alba, sucrose, talc, gelatin, agar, pectin, acacia, magnesium stearate, and stearic acid. Liquid carriers include syrup, peanut oil, olive oil, saline and water. Suppositories are prepared from standard bases such as polyethylene glycol and cocoa butter.

The method of this invention of antagonizing excitatory amino acid receptors comprises administering internally to a subject expected to be benefited thereby an effective amount of the invented ACPA isomer. Doses of this isomer included in the invented methods and pharmaceutical compositions are an efficacious, nontoxic quantity selected from the range of 0.01 to 100 mg/kg of active compound, preferably 0.1 to 50 mg/kg. Persons skilled in the art using routine clinical testing are able to determine optimum doses. The desired dose is administered to a subject from 1 to 6 or more times daily, orally, rectally, parenterally, or topically.

The unexpected greater potency of the invented isomer is shown by the data in Tables 1 and 2, below. The data reported were obtained using mixtures which were enriched in the stated isomer but were less than about 95% pure. Also, it is believed that cis isomer A is the 2R, 4R, 5S isomer. The invented isomer thus is cis isomer A even if subsequent analysis shows it to be other than the 2R, 4R, 5S isomer. In these tables CPP is 4-(3-phosphonopropyl)-2-piperazine carboxylic acid and CGS-19755 is cis-4-(phosphonomethyl)-2-piperidinecarboxylic acid.

TABLE 1

POTENCY TO INHIBIT NMDA-INDUCED SEIZURES OR IMPAIR ROTOROD PERFORMANCE FOLLOWING ICV ADMINISTRATION

| COMPOUND | $ED_{50}$ | $TD_{50}$ | $TD_{50}/ED_{50}$ |
| --- | --- | --- | --- |
| | (mg/kg) | | |
| CGS-19755 | 2.64 | 17 | 6.4 |
| (±) CPP | 2.20 | 10 | 4.5 |
| cis isomer A | 1.05 | 32 | 30.5 |
| cis isomer B | 25–50 | >150 | |
| cis isomer C | 32.5 | >150 | >4.5 |
| cis isomer D | 39.5 | >250 | >3.8 |
| trans isomers E + F | >100 | >100 | — |
| trans isomers G + H | >100 | >100 | — |

The procedure for determining the $ED_{50}$ for inhibiting NMDA-induced seizures and impairing rotorod performance is described in Example 3. The Table 1 data show that the cis isomer A is at least 25-fold more potent than the next most potent isomer in producing these in vivo effects.

TABLE 2

POTENCY TO INHIBIT SPECIFIC BINDING OF [3H]CGS-19755 TO RAT FOREBRAIN MEMBRANES

| Compound | IC50 (uM) |
| --- | --- |
| (±) CPP | 0.19 ± 0.015 |

TABLE 2-continued

POTENCY TO INHIBIT SPECIFIC BINDING OF
[3H]CGS-19755 TO RAT FOREBRAIN MEMBRANES

| Compound | IC50 (uM) |
|---|---|
| cis isomer A | 0.27 ± 0.012 |
| cis isomer B | 5.55 ± 1.25 |
| cis isomer C | 2.39 ± 0.85 |
| cis isomer D | 2.64 ± 0.85 |

The procedure for determining the binding potencies reported in Table 2 is described in Example 4. The Table 2 data show that the cis isomer A is approximately 8-fold more potent than cis isomer C, the next most potent isomer.

The following examples are illustrative of preparation and testing of the invented isomer of ACPA. In these Examples, the compounds designated by roman and arabic numerals are shown in Schemes I and II, above, respectively.

Compound I 1R, 2S-Methyl (hydrogen)-cis-1,2-cyclohexane diacetate

A solution of 1R, 2S-Methyl (hydrogen)-1,2-cis-cyclohex-4-ene diacetate (41 g; 0.19 mol) in ethanol (210 ml) was treated with 6 g of 5% palladium on carbon and hydrogenated in a Paar hydrogenator for 5 hr at 55 psi pressure of hydrogen. The solution was filtered through Celite to remove the catalyst and concentrated to deliver 39.4 g (95%) of the cyclohexane half-ester as a colorless oil.

$^1$H NMR (CDCl$_3$): d 1.25-1.53 (m, 8H); 2.21-2.28 (m, 6H); 3.67 (s, 3H).

IR (neat): 2923, 2862, 2666, 1736, 1704, 1440, 1293, 1242, 1165, 1113, 1016, 946 cm$^{-1}$.

Compound II

Diborane (187 ml of a 1.0M solution in THF; 0.187 mol) was added in a dropwise manner to a cooled (0° C.) solution of the half ester (36.83 g; 0.17 mol) in THF (200 ml). After the addition was complete the reaction mixture was allowed to slowly come to room temperature overnight. The reaction was quenched by the addition of 500 ml of 1N HCl and stirred for an additional 45 minutes. The product was extracted into 3×300 ml of ethyl acetate and the organic layers were washed with brine, dried (MgSO$_4$) and freed of solvent. The hydroxy ester was obtained as a colorless oil (32.8 g; 96%).

$^1$H NMR (CDCl$_3$): d 1.23-1.76 (m, 11H); 2.12-2.27 (m, 3H); 3.70 (m, 5H).

IR (neat): 3428, 2926, 2862, 1736, 1437, 1291, 1167, 1054, 1013 cm$^{-1}$.

Compound III (Silyl ether III)

A mixture of hydroxy ester II (8.4 g; 42 mmol), tert-butyldimethylsilyl chloride (7.83 g; 50.4 mmol); dimethylaminopyridine (518 mg; 4.2 mmol) and triethylamine (4.67 g; 46.2 mmol) in dimethylformamide (30 ml) was stirred overnight at room temperature. Water (30 ml) was added and the product was extracted into 3×50 ml of ethyl acetate. The combined organic layers were washed with brine, dried (MgSO$_4$) and concentrated. The crude product was purified by column chromatography, eluting with 3-5% ethyl acetate in hexane, to obtain 11.2 g (80%) of the product as a clear liquid.

$^1$H NMR (CDCl$_3$): d 0.01 (s, 6H); 0.84 (s, 9H); 1.25-1.57 (m, 11H); 2.20 (m, 1H); 2.23 (d, 1H); 3.54-3.61 (m plus s, 5H).

IR (neat): 2926, 2857, 1740, 1463, 1434, 1388, 1360, 1255, 1105, 1100, 1007, 938, 825cm$^{-1}$.

Compound IV (Aldehyde IV)

A solution of ester III (2.50 g; 8.0 mmol) in 40 ml of toluene was cooled to −78° C. and treated with diisobutylaluminum hydride (6.1 ml of a 1.5M solution; 9.2 mmol). The mixture was stirred for 2 hours at −78° C. and then poured into 30 ml of an ice-cold saturated aqueous solution of sodium-potassium tartrate. The layers were separated and the aqueous layer was washed with 2×20 ml of ethyl acetate. The combined organic layers were washed with brine, dried (MgSO$_4$) and freed of solvent. The residue was purified on a silica gel column eluting with 1-5% ethyl acetate in hexane to obtain 1.63 g (72%) of the product as a light oil.

$^1$H NMR (CDCl$_3$): d 0.05 (s, 6H); 0.89 (s, 9H); 1.26-1.74 (m, 11H); 2.23-2.38 (m, 3H); 3.65 (m, 2H); 9.76 (d, 1H).

IR (neat): 2931, 2707, 1730, 1468, 1388, 1255, 1100, 836, 776 cm$^{-1}$.

Compound V (Hydroxy hydantoin V)

Aldehyde IV (8.0 g; 28.1 mmol) was dissolved in 65 ml of ethanol, and a solution of sodium cyanide (3.09 g; 61.8 mmol) and ammonium carbonate (13.5 g; 140 mmol) in water (65 ml) was added. This mixture was sealed in a glass tube and heated in an oil bath at 90° C. for 18 hours. After cooling the reaction mixture was poured into a 500 ml beaker and acidified to pH 1 with HCl. After stirring at room temperature for one hour the mixture was cooled in an ice-bath and the precipitate was collected by vacuum filtration. The collected solid was washed with ice-cold water until the washings were pH 5-6, then washed with cold ether and ethyl acetate. The solid product was dried under vacuum to obtain 3.71 g (68%) of the hydroxy hydantoin as a white solid, mp 209° C.

$^1$H NMR (DMSO-d6): d 1.04-1.69 (m, 14H); 3.30-3.42 (m, 2H); 3.96 (d, 1H); 4.32 (t, 1H); 8.02 (d, 1H); 10.57 (br d, 1H).

IR (KBr): 3309, 2928, 2757, 1730, 1715, 1421, 1314, 1203, 1059 cm$^{-1}$.

Compound VI (Mesylate VI)

Hydroxy hydantoin V (4.8 g; 20 mmol) was dissolved in pyridine (30 ml). After cooling this solution to 0° C., methanesulfonyl chloride (2.75 g; 22 mmol) was added neat in a slow, dropwise fashion. After the addition was complete the reaction mixture was stirred for 15 minutes at 0° C. and 2 hours at room temperature. The pyridine was removed in vacuo and the residue was dissolved in 80 ml of chloroform. The chloroform phase was washed with 30 ml of 1N HCl, dried (MgSO$_4$) and freed of solvent to obtain 6.0 g (94%) of the product as a white solid, mp 150° C.

$^1$H NMR (DMSO-d6): d 1.28-1.78 (m, 14H); 3.14 (s, 3H); 3.96 (t, 1H); 4.18 (m, 2H); 8.03 (d, 1H); 10.58 (d, 1H).

IR (KBr): 3286, 2928, 1769, 1416, 1357, 1177 cm$^{-1}$.

Compound VII (Bromide VII)

Mesylate VI (6.0 g; 18.87 mmol) was dissolved in 50 ml of N,N-dimethylformamide containing 5.21 g (60 mmol) of lithium bromide. This mixture was stirred overnight at 45° C. under an argon atmosphere. After cooling to 0° C., cold water (80 ml) was added to the reaction mixture and the resulting precipitate was collected by filtration and washed with 2×30 ml of ice-cold water and 2×30 ml of ether. The product was dried under vacuum to obtain 4.55 g (80%) of bromide VII as a white solid.

$^1$H NMR (DMSO-d6): d 1.22–1.71 (m, 14H); 3.61 (m, 2H); 3.99 (d, 1H); 8.04 (d, 1H); 10.58 (d, 1H).

IR (KBr): 3541, 3304, 3219, 2926, 2363, 1772, 1728, 1427, 774, 648 cm$^{-1}$.

Compound VIII (Phosphonoethyl hydantoin VIII)

Diethyl phosphite (2.12 g; 15.34 mmol) in tetrahydrofuran (10 ml) was added dropwise to a stirred slurry of sodium hydride (506 mg of an 80% oil dispersion; 16.87 mmol) in tetrahydrofuran (20 ml), at room temperature and under an argon atmosphere. After the addition was complete and gas evolution had ceased the mixture was stirred for 1.5 hours at room temperature. Bromide VII (1.5 g; 4.95 mmol) was added via syringe as a dimethylformamide solution (20 ml). The mixture was stirred for one hour at room temperature and then heated to 80° C. for 24 hours. After cooling, the reaction was quenched by the addition of saturated aqueous ammonium chloride (20 ml) and extracted into 100 ml of ethyl acetate. The organic phase was washed with 3×50 ml of brine, dried (MgSO$_4$) and freed of solvent. The residue was purified on a silica gel column, using a gradient elution from 1% methanol in methylene chloride to 10% methanol in methylene chloride. The product (1.50 g; 84%) was obtained as a white foamy glass.

$^1$H NMR (CDCl$_3$): d 1.10–2.01 (m, 22H); 4.02–4.16 (m, 5H); 7.15–7.26 (d, 1H); 9.64 (b, 1H).

IR (CDCl$_3$): 3440, 3155, 2934, 2263, 1772, 1725, 1468, 1383, 1211, 1095 cm$^{-1}$.

Compound IX (Carbamoyl acid IX)

Hydantoin VIII was converted to the carbamoyl derivative by reaction with the enzyme D-hydantoinase. Carbamoyl IX was obtained in yields of ca. 60% as a white crystalline solid after recrystallization from water. X-ray diffraction analysis of this compound verified that it was of the 2R, 4R, 5S configuration.

$^1$H NMR (CDCl$_3$): d 1.27–2.01 (m, 22H); 3.49 (s, 2H); 4.17–4.22 (m, 4H); 4.48 (d, 1H); 6.58 (br, 1H).

Electron impact mass spectrum: m/e 379 (MH+), 364, 336, 335, 291, 263.

Compounds X and XI (Amino acid X and final product XI)

Carbamoyl acid IX is chemically cleaved to the free amino acid X using nitrous acid as described in the literature cited above. Cleavage of the phosphonate esters of X to give XI is achieved using either bromo- or iodotrimethylsilane. Compound X (1 mmol) in methylene chloride/acetonitrile (10 ml) is treated with the halotrimethylsilane (10 mmol). This mixture is stirred for 16 hours at room temperature and then evaporated to dryness. The residue is partitioned between water and chloroform. The aqueous layer is made neutral (pH 7) and concentrated in vacuo; the product can be purified by ion exchange on a Dowex 50W-Xb column. Compound XI is obtained as the hydrate.

EXAMPLE 2

Compound 5 (dehydro half-ester 5)

1-Methyl hydrogen (1S,2R)-1,2-cyclohex-4-enedicarboxylate (10 g; 55.34 mmol) was dissolved in ethanol (150 ml) and hydrogenated in the presence of 5% palladium on carbon for four hours at 50 psi pressure of hydrogen. The reaction mixture was filtered through Celite to remove the catalyst and concentrated in vacuo to obtain the product as a white solid, 9.48 g (95%), mp 60°–62° C.

$^1$H NMR (CDCl$_3$): d 1.37–2.15 (m, 8H); 2.85 (br t, 2H); 3.70 (s, 3H); 10.15 (br, 1H).

IR (neat): 1743, 1697 cm$^{-1}$.

Compound 6 ((−)-1R, 2S-lactone 6)

Half ester 5 (1.04 g; 5.59 mmol) was dissolved in 20 ml of dry tetrahydrofuran in a 100 ml flask. After cooling this solution to −78° C., with stirring and under an argon atmosphere, lithium triethylborohydride (18 ml of a 1.0M solution in tetrahydrofuran, 18 mmol, 3.2 eq) was added dropwise via syringe. The reaction mixture was allowed to slowly warm to room temperature over the course of four hours and was quenched by the addition of 30 ml of 1N HCl. After stirring the mixture for an additional 1 hour the product was extracted into 3×50 ml of ether. The ether portions were washed with brine, dried (MgSO$_4$) and freed of solvent. The product was purified on a silica gel column eluting with 5% ethyl acetate in hexane to obtain the product as a clear oil, 550 mg (70%).

$^1$H NMR (CDCl$_3$): d 1.18–1.31 (m, 3H); 1.55–1.70 (m, 3H); 1.78–1.83 (m, 1H); 2.15 (d, 1H); 2.40–2.50 (m, 1H); 2.60–2.68 (m, 1H); 3.95–4.00 (d, 1H); 4.20 (d of d, 2H).

IR (neat): 1770 cm$^{-1}$.

Compound 7 (Hydroxy vinylphosphonate 7)

Tetraethyl methylenebisphosphonate (4.32 g; 14.99 mmol) was added dropwise as a tetrahydrofuran solution (10 ml) to a stirred suspension of sodium hydride (660 mg of a 60% oil dispersion; 16.5 mmol) in THF (15 ml). After gas evolution had ceased the mixture was stirred at room temperature for 2 hours and then cooled to −78° C. In a separate flask, a solution of lactone 6 (1.0 g; 7.14 mmol) in toluene (15 ml), cooled to −78° C., was treated with diisobutylaluminum hydride in toluene via syringe (5.7 ml of a 1.5M solution; 8.55 mmol). After stirring this mixture for 45 minutes, it was quenched by the addition of 50 ml of methanol, and this mixture was added via canula to the THF solution of the anion. The resulting mixture was stirred for 4 hours at −78° C.; tert-butyldimethylsilyl chloride (1.18 g; 7.5 mmol) in 15 ml of THF was then added and the mixture was stirred overnight while slowly warming to room temperature. It was quenched by the successive addition of saturated aqueous ammonium chloride (20 ml) and 1N HCl (50 ml). The product was extracted into ethyl acetate and the organic phase was washed with brine, dried (MgSO$_4$) and freed of solvent. The product was purified on a silica gel column utilizing a gradient elution (40% hexane in ethyl acetate to pure ethyl acetate). The product was obtained as a clear viscous oil, 1.40 g (71%).

$^1$H NMR (CDCl$_3$): d 1.25–2.05 (m+t, 15H); 2.65–2.75 (m, 1H); 3.48 (d, 2H); 3.98–4.15 (m, 4H); 5.65–5.81 (m, 1H); 6.83–7.03 (m, 1H).

IR (neat): 3400, 2982, 2926, 2861, 1627, 1447, 1391, 1229, 1041, 956 cm$^{-1}$.

Compound 8 (Hydroxy phosphonoethyl compound 8)

A mixture of vinylphosphonate 7 (2.70 g) and 5% palladium on carbon (600 mg) in ethanol (30 ml) was hydrogenated at 50 psi pressure of hydrogen for 4 hours. The reaction mixture was filtered through Celite and concentrated to obtain 8 as a clear oil, 2.70 g (99%).

$^1$H NMR (CDCl$_3$): d 1.21–1.84 (m, 20H); 2.60 (br, 1H); 3.47–3.60 (m, 2H); 4.05–4.14 (m, 4H).

IR (neat): 3400, 2980, 2924, 2859, 1448, 1391, 1230, 1054, 959, 828, 784 cm$^{-1}$.

Compound 9 (Phosphonoethyl aldehyde 9)

A solution of oxalyl chloride (1.34 g; 10.55 mmol) in methylene chloride (25 ml) was cooled to −60° C. and treated with 2 ml of DMSO (28.18 mmol). After stirring for 10 minutes, alcohol 8 (2.63 g; 9.46 mmol) was added as a methylene chloride solution (5 ml). After stirring this mixture for an additional 15 minutes triethylamine (6.6 ml; 47.4 mmol) was added and the mixture was stirred for 5 minutes at −60° C. and 30 minutes at room temperature. Water (50 ml) was added, the layers were separated, and the organic phase was washed with brine, dried (MgSO$_4$) and the solvent removed in vacuo. The crude product was purified on a silica gel column eluting with ethyl acetate to obtain 2.20 g (84%) of the aldehyde as a clear thick oil.

$^1$H NMR (CDCl$_3$): d 1.29–1.77 (m, 13H); 2.43–2.55 (m, 1H); 4.06–4.12 (m, 4H); 9.79 (s, 1H).

IR (neat): 3456, 2980, 2931, 2859, 2715, 1720, 1450, 1391, 1242, 1036, 959, 831, 789 cm$^{-1}$.

Compounds 11a and 11b (N-acetyl amino esters 11a and 11b)

A solution of methyl 2-acetylamino-2-(dimethoxyphosphinyl)acetate (1.82 g; 7.61 mmol) in THF (50 ml) was added to a stirred slurry of sodium hydride (304 mg of a 60% oil dispersion; 7.60 mmol) in 20 ml of THF at room temperature. After stirring this mixture for 1 hour, the aldehyde was added as a THF solution (20 ml). The mixture was stirred at room temperature for 24 hours, quenched by the addition of 20 ml of saturated aqueous ammonium chloride, and acidified with 1N HCl until the pH was 2. It was extracted into ethyl acetate and the ethyl acetate portions were washed with brine, dried and freed of solvent. The residue was purified on a silica gel column eluting with ethyl acetate. Dehydro N-acetyl amino ester 10 was obtained contaminated with unreacted phosphonate reagent; 640 mg of this impure product was obtained.

This impure material was hydrogenated in the presence of 5% palladium on carbon (200 mg) in 30 ml of ethanol under 50 psi pressure of hydrogen for 4 hours. The mixture was filtered through Celite and freed of solvent. Purification of the crude residue on a silica gel-60 column, eluting with 5% methanol in ethyl acetate, delivered a total of 260 mg (8.7% overall) of a pure mixture of 11a and 11b.

$^1$H NMR (CDCl$_3$) (11a+11b): d 1.15–1.88 (m, 20H); 2.02 (s, 3H); 3.73 (s, 3H); 4.00–4.19 (m, 4H); 4.55–4.68 (m, 1H); 5.98 and 6.38 (br d's, 1H total).

Enzymatic resolution of 11a and 11b; compounds 11a and 12.

The mixture of esters 11a and 11b (260 mg total) was dissolved in pH 7.4 phosphate buffer and stirred at room temperature. Subtilisin A (Novo Biolabs, 30 mg) was added and the mixture was stirred overnight. The pH was brought back to 7.4 by the dropwise addition of 0.2M NaOH. The mixture was diluted with water, transferred to a separatory funnel, and extracted with 3×75 ml of ethyl acetate. The ethyl acetate portions were dried (MgSO$_4$) and freed of solvent to deliver 100 mg of 11a.

The aqeous phase was made acidic (pH 1) with 1N HCl and extracted with 3×75 ml of ethyl acetate. After drying and removal of the solvent 50 mg of acid 12 was obtained.

11a: $^1$H NMR (CDCl$_3$): d 1.24–1.88 (m, 20H); 2.04 (s, 3H); 3.74 (s, 3H); 4.03–4.15 (m, 4H); 4.57 (t of d, 1H); 6.34 (br d, 1H).

8: $^1$H NMR (CDCl$_3$): d 1.24–1.84 (m, 20H); 2.07 (s, 3H); 4.05–4.10 (m, 4H); 4.66–4.68 (m, 1H); 6.46 (br d, 1H).

Hydrolysis of 11a and 12 to 2R, 4R, 5S and 2S, 4R, 5S isomers, respectively.

Compounds 11a and 12 were each refluxed vigorously in 6N HCl overnight. The solutions were concentrated in vacuo and in each case the crude material was dissolved in ethanol and treated with propylene oxide to obtain the free bases. Small amounts of each of the two final products were obtained. HPLC analysis of the products, using racemic NPC 12626 as a reference, confirmed their identities as two diastereomeric cis isomers of NPC ACPA.

EXAMPLE 3

Anticonvulsant Studies

The potency of the isomers of APCA to inhibit NMDA-induced seizures was evaluated using male CF-1 mice. All drugs were dissolved in isotonic saline and the pH adjusted to neutrality using NaOH. The test compounds were injected intracerebroventricularly (i.c.v.) in a final volume of 5 ml. N-Methyl-D-aspartate (250 mg/kg of body weight) was dissolved in saline (1% v/w of body weight) and injected intraperitoneally (i.p.) 15 minutes following the administration of the test agent. Mice were observed for 30 minutes following the administration of the chemical convulsant and scored as present or absent. NMDA-induced seizures were defined as presence of tonic/clonic activity accompanied by hindlimb extension and death.

Rotorod

Animals used for seizure studies were evaluated for motor impairment using the rotorod test. Before use all animals were tested for their ability to maintain equilibrium for 60 seconds on a 1-inch knurled bar rotating at a speed of 6 to 7 rpm. Each animal was given three separate trials. Animals performing the task in any of the three trials were used for further study.

Animals were tested for impairment 10 minutes after i.c.v. administration of the test agent and 5 minutes before administration of the seizure-inducing agent. Each animal was tested on a maximum of three trials; completion of any one of the trials was screened as passing.

EXAMPLE 4

Binding Studies

The potency of compounds to inhibit the specific binding of [$^3$H]CGS-19755 (specific activity 50.5 Ci/mmol, New England Nuclear, Boston, Mass.) to NMDA receptors was performed as described by Ferkany et al.

(*J. Pharmacology and Experimental Therapeutics*, 1989, 250:100–109). Briefly, animals were sacrificed by decapitation, the forebrain removed immediately and the "buffy coat" prepared as described by Enna and Snyder (Enna, S. and Snyder, S. H., *Molecular Pharmacology*, 1977, 13:422–433). Crude synaptic membranes were stored frozen ($-20°$ C.) until used. On the day of the assay, membranes were thawed to room temperature and homogenized in 20 vol (w/v) of assay buffer. The homogenate was centrifuged ($48,000 \times g$; 10 min; $4°$ C.), the supernatant decanted and the pellet resuspended as before. The procedure was repeated until the tissue had been washed 4 times to remove endogenous inhibitors.

For assay, the final pellet was resuspended in sufficient buffer (Tris HCl, 0.05M, pH 7.1, $23°$ C.) to yield a tissue concentration of 0.2 mg of protein per ml. Two-milliliter portions of the suspension were added in duplicate to tubes containing ligand (final concentration $=4.62 \times 10^{-9}$M) and the compound of interest (40 ml). After an incubation of 20 min ($23°$ C.), the reaction was terminated by centrifugation, the supernatant was decanted and the pellets washed rapidly and superficially with $2 \times 2.5$ ml of ice-cold buffer. Tissue was solubilized in Protosol (0.5 ml, New England Nuclear, Boston, Mass.) and after the addition of scintillant, radioactivity was determined using standard procedures.

Non specific binding was determined using L-glutamate at a final concentration of $10^{-3}$M. Routinely, $IC_{50}$s were determined using 8–12 concentrations of inhibitor.

While the preferred embodiments of the invention are illustrated by the above, it is to be understood that the invention is not limited to the precise instructions contained herein and that the right to all modifications within the scope of the following claims is reserved.

What is claimed is:

1. The 2R, 4R, 5S isomer of the compound 2-amino-4,5-(1,2-cyclohexyl)-7-phosphonoheptanoic acid or any pharmaceutically acceptable salt or hydrate of the isomer wherein the isomer or salt or hydrate of the isomer is substantially free from other stereoisomers of the compound.

2. A pharmaceutical composition useful for antagonizing excitatory amino acid receptors comprising the 2R, 4R, 5S isomer of the compound 2-amino-4,5-(1,2-cyclohexyl)-7-phosphonoheptanoic acid or any pharmaceutically acceptable salt or hydrate of the isomer wherein the isomer or salt or hydrate of the isomer is substantially free from other stereoisomers of the compound.

3. A method for antagonizing excitatory amino acid receptors in mammals that comprises administering to a subject an effective amount of the 2R, 4R, 5S isomer of the compound 2-amino-4,5-(1,2-cyclohexyl)-7-phosphonoheptanoic acid or any pharmaceutically acceptable salt or hydrate of the isomer wherein the isomer or salt or hydrate of the isomer is substantially free from other stereoisomers of the compound.

* * * * *